United States Patent [19]

Laurent et al.

[11] Patent Number: 4,970,080

[45] Date of Patent: Nov. 13, 1990

[54] METHOD OF TREATING ASCITES IN ANIMALS

[75] Inventors: Sebastian M. Laurent, Greenwell Springs; Robert N. Sanders, Baton Rouge, both of La.

[73] Assignee: Ethyl Corporation, Baton Rouge, La.

[21] Appl. No.: 304,222

[22] Filed: Jan. 30, 1939

Related U.S. Application Data

[60] Continuation-in-part of Ser. No. 801,596, Nov. 25, 1985, Pat. No. 4,847,085, which is a continuation-in-part of Ser. No. 71,572, Jun. 5, 1985, abandoned, which is a division of Ser. No. 475,370, Mar. 14, 1983, Pat. No. 4,556,564.

[51] Int. Cl.$^5$ .............................................. A61K 33/06
[52] U.S. Cl. .................................................. 424/684
[58] Field of Search ........................................ 424/684

[56] References Cited

FOREIGN PATENT DOCUMENTS 59-203450 of 0000 Japan .

Primary Examiner—Frederick E. Waddell
Attorney, Agent, or Firm—Robert J. Baran; Walter A. Hackler

[57] ABSTRACT

Methods of (a) improving the quality of the bones and/or increasing the bone strength and/or the blood quality of and/or (b) treating ascites and/or fatty liver syndrome in animals, including humans, cattle, sheep, goats, swine, cats, dogs and poultry without deleterious effects on the animals or products of the animals by adding small effective amounts of zeolite to the feed of the animals or directly to the animals in the form of a capsule, tablet or the like.

13 Claims, No Drawings

METHOD OF TREATING ASCITES IN ANIMALS

CROSS-REFERENCE TO RELATED APPLICATIONS

This is a Continuation-In-Part U.S. Ser. No. 801,596 filed Nov. 25, 1985, now U.S. Pat. No. 4,847,085 which is a Continuation-In-Part of U.S. Ser. No. 741,572 filed June 5, 1985, now abandoned which is a Division of U.S. Ser. No. 475,370, filed Mar. 14, 1983, now U.S. Pat. No. 4,556,564.

BACKGROUND OF THE INVENTION

The present invention is in the general field of animal therapy and relates to the treatment and prevention of bone disorders such as osteoporosis, osteoarthritis and the like, especially in humans.

The invention especially relates to the use of metal alumino silicates such as zeolites, particularly Zeolite A, in the treatment of the aforesaid bone disorders.

It is therefore an important object of the present invention to provide a therapy for the treatment of the aforesaid bone disorders utilizing zeolites.

In the poultry industry, one of the problems prevalent throughout the industry is the legs of male breeders. The productive life of a female broiler breeder, for example, is nine months while the male broiler breeders have to be replaced after six months or sometimes even earlier. This early replacement is necessitated because of a breakdown in the legs of the males, thus limiting the frequency of mating. Male mortality rate is also about three to four times that of the female rate and this high rate is largely associated with leg problems. One of the major causes of the leg problems in poultry is a disease called tibial dyschondroplasia. Other less frequent causes are femur head necrosis and twisted leg disease.

It is therefore an important object of the present invention to inhibit the formation in poultry of the disease, tibial dyschondroplasia or other bone related diseases.

Applicants' parent application discloses the effectiveness of including a small amount of Zeolite A in the feed formulation of laying hens in increasing the quality or strength of the egg shells of the eggs produced by the hens without decreasing egg production or having any deleterious effect on the eggs themselves. Application Ser. No. 475,370 is hereby incorporated herein in its entirety.

Over the years, a wide variety of experiments have been conducted throughout the world utilizing zeolites of many different types in the feeding of animals for varying reasons. Most of these experiments have been in animal nutrition or in increasing the production of food animals or their food products. Most of the animals fed zeolites were poultry, cattle, sheep and swine. Zeolites fed to the animals were mainly naturally occurring zeolites or those zeolites found in nature. Although some degree of success in some areas was achieved, most of the results were unfavorable.

An article by C. Y. Chung, et al. from Nongsa Sihom Youngu Pogo 1978, 20 (Livestock), pp. 77-83 discusses the effects of cation exchange capacity and particle size of zeolites on the growth, feed efficiency and feed materials utilizability of broilers or broiling size chickens. Supplementing the feed of the broilers with naturally occurring zeolites, such as clinoptilolite, some increase in body weight gain was determined. Chung, et al. also reported that earlier results at the Livestock Experiment Station (1974, 1975, 1976 - Suweon, Korea) showed that no significant difference was observed when 1.5, 3, and 4.5 percent zeolite was added to chicken layer diets.

U.S. Pat. No. 3,836,676 issued to Chukei Komakine in 1974 discloses the use of zeolites as an adsorbent for adhesion moisture of ferrous sulfate crystals in an odorless chicken feed comprising such crystals and chicken droppings. The results were said to be no less than those in the case where chickens were raised with ordinary feed.

Experiments have been in progress in Japan since 1965 on the use of natural zeolite minerals as dietary supplements for poultry, swine and cattle. Significant increases in body weight per unit of feed consumed and in the general health of the animals was reported (Minato, Hideo, Koatsugasu 5:536, 1968). Reductions in malodor were also noted.

Using clinoptilolite and mordenite from northern Japan, Onagi, T. (Rept. Yamagata Stock Raising Inst. 7, 1966) found that Leghorn chickens required less food and water and gained as much weight in a two-week trial as birds receiving a control diet. No adverse effects on health mortality were noted. The foregoing Japanese experiments were reported by F. A. Mumpton and P. H. Fishman in the *Journal of Animal Science*, Vol. 45, No. 5 (1977), pp. 1188–1203.

Canadian Patent No. 939,186 issued to White, et al. in 1974 (U.S. Pat. No. 4,393,082) issued July 12, 1983) discloses the use of zeolites having exchangeable cations as a feed component in the feeding of urea or biuret non-protein nitrogen (NPN) compounds to ruminants, such as cattle, sheep and goats. Natural and synthetic as well as crystalline and non-crystalline zeolites are disclosed. Zeolites tested using in vitro techniques included natural zeolites, chabazite and clinoptilolite and synthetic zeolites X, Y, F, J, M, Z, and A. Zeolite F was by far the most outstanding and Zeolite A was substantially ineffective.

An article by W. L. Willis, et al. entitled "Evaluation of Zeolites Fed to Male Broiler Chickens" published in *Poultry Science*, Volume 61, Number 3, p. 438–442 (March, 1982) discloses the feeding of natural zeolites such as clinoptilolite to male broiler chickens in amounts of 1, 2 and 3 weight percent.

In a study of the University of Georgia, both broilers and layers were fed small amounts (about 2%) of clinoptilolite, a naturally occurring zeolite from Tilden, Tex. The egg shells from the hens receiving zeolite were slightly more flexible as measured by deformation, slightly less strong as measured by Instron breaking strength, and had a slightly lower specific gravity. The differences in egg shell quality were very small. This type of zeolite was ineffective in producing a stronger egg shell. An article written by Larry Vest and John Shutze entitled "The Influence of Feeding Zeolites to Poultry Under Field Conditions" summarizing the studies was presented at Zeo-Agriculture '82.

A study of H. S. Nakaue of feeding White Leghorn layers clinoptilolite, reported in 1981 Poultry Science 60:944–949, disclosed no significant differences in egg shell strength between hens receiving the zeolite and hens not receiving the zeolite.

European Patent Application No. 011992 published Sept. 26, 1984 discloses the feeding of the natural zeolite, chabazite, to poultry, namely turkeys. In a test utilizing 480 tom turkeys, those turkeys fed 2 weight percent chabazite ore showed improved weight gain and feed efficiency over those turkeys fed similar amounts of sodium exchanged Zeolite A and calcium exchanged Zeolite A; however, the turkeys fed zeolites showed an increase in mortality rate over those turkeys in which no zeolites were fed. The turkeys fed sodium exchanged Zeolite A showed significantly less weight gain and less feed efficiency than those turkeys fed no zeolites at all and the turkeys fed calcium exchanged Zeolite A showed about the same weight gain as the control, but had even less feed efficiency than the turkeys fed the sodium exchanged Zeolite A.

Japanese Patent No. 59-203450 published Nov. 17, 1984 describes the use of synthetic metal aluminosilicates, preferably type A, type P, type X or type Y zeolites, as feed additives for livestock, pets, cultured fish, etc. with active ingredients consisting of basicity-adjusted aluminosilicates to an equilibrium pH of 10.5 or less. The feed additivies are said to have a digestion-regulating effect, i.e., a high antacid effect in the pH range of 3 to 5. They also are said to appear to be superior as $Co++$ donors and donors of other minerals. In a single experiment of 100 piglets, using 2 weight percent calcium aluminosilicate, either amorphous or type A zeolite, no significant differences between the two forms were observed. Body weight for piglets fed the calcium zeolites showed an increase but feed utilization weight was down slightly.

Zeolites are crystalline hydrated aluminosilicates of alkali and alkaline earth cations, having infinite, three-dimensional structures.

Zeolites consist basically of a three-dimensional framework of $SiO_4$ and $AlO_4$ tetrahedra. The tetrahedra are crosslinked by the sharing of oxygen atoms so that the ratio of oxygen atoms to the total of the aluminum and silicon atoms is equal to two or $O/(Al+Si)=2$. The electrovalence of each tetrahedra containing aluminum is balanced by the inclusion in the crystal of a cation, for example, a sodium ion. This balance may be expressed by the formula $Al/Na=1$. The spaces between the tetrahedra are occupied by water molecules prior to dehydration.

There are a number of different types of zeolites. Some zeolites are found in nature and are made synthetically. Other zeolites are made only synthetically. Zeolite A is not found in nature and is made only synthetically.

Zeolite A may be distinguished from other zeolites and silicates on the basis of their composition and x-ray powder diffraction patterns and certain physical characteristics. The x-ray patters for these zeolites are described below. The composition and density are among the characteristics which have been found to be important in identifying these zeolites.

The basic formula for all crystalline sodium zeolites may be represented as follows:

$$Na_2O.Al_2O_3.xSiO_2.yH_2O.$$

In general, a particular crystalline zeolite will have values for "x" and "y" that fall in a definite range. The value "x" for a particular zeolite will vary somewhat since the aluminum atoms and the silicon atoms occupy essentially equivalent positions in the lattice. Minor variations in the relative number of these atoms do not significantly alter the crystal structure or physical properties of the zeolite. For Zeolite A, the "x" value normally falls within the range $1.85\pm0.5$.

The value for "y" is not necessarily an invariant for all samples of zeolites. This is true because various exchangeable ions are of different size, and, since there is no major change in the crystal lattice dimensions upon ion exchange, the space available in the pores of the zeolite to accomodate water molecules varies.

The average value of "y" for Zeolite A is 5.1. The formula for Zeolite A may be written as follows:

$$1.0\pm0.2\ Na_2O.Al_2O_3.1.85\pm0.5\ SiO_2.yH_2O.$$

In the formula, "y" may be any value up to 6.

An ideal Zeolite A has the following formula:

$$(NaAlSiO_4)_{12}.27H_2O$$

Among the ways of identifying zeolites and distinguishing them from other zeolites and other crystalline substances, the x-ray powder diffraction pattern has been found to be a useful tool. In obtaining the x-ray powder diffraction patterns, standard techniques are employed. The radiation is the Kd doublet of copper and a Geiger counter spectrometer with a strip chart pen recorder is used. The peak heights, I, and the positions as a function of $2\theta$ where $\theta$ is the Bragg angle, are read from a spectrometer chart. From these, the relative intensities, $100\ I/I_o$, where $I_o$ is the intensity of the strongest line or peak and d the interplanar spacing in angstroms corresponding to the recorded lines are calculated.

X-ray power diffraction data for a sodium Zeolite A are given in Table I.

TABLE I

| X-RAY DIFFRACTION PATTERN FOR ZEOLITE A | | |
|---|---|---|
| $H^2 + k^2 + l^2$ | d (Å) | $\dfrac{100\ I}{I_o}$ |
| 1 | 12.29 | 100 |
| 2 | 8.71 | 70 |
| 3 | 7.11 | 35 |
| 4 | 6.15 | 2 |
| 5 | 5.51 | 25 |
| 6 | 5.03 | 2 |
| 8 | 4.36 | 6 |
| 9 | 4.107 | 35 |
| 10 | 3.895 | 2 |
| 11 | 3.714 | 50 |
| 13 | 3.417 | 16 |
| 14 | 3.293 | 45 |
| 16 | 3.078 | 2 |
| 17 | 2.987 | 55 |
| 18 | 2.904 | 10 |
| 20 | 2.754 | 12 |
| 21 | 2.688 | 4 |
| 22 | 2.626 | 20 |
| 24 | 2.515 | 6 |
| 25 | 2.464 | 4 |
| 26 | 2.414 | >1 |
| 27 | 2.371 | 3 |
| 29 | 2.289 | 1 |
| 30 | 2.249 | 3 |
| 32 | 2.177 | 7 |
| 33 | 2.144 | 10 |
| 34 | 2.113 | 3 |
| 35 | 2.083 | 4 |
| 36 | 2.053 | 9 |
| 41 | 1.924 | 7 |
| 42 | 1.901 | 4 |
| 44 | 2.858 | 2 |
| 45 | 1.837 | 3 |
| 49 | 1.759 | 2 |
| 50 | 1.743 | 13 |
| 53 | 1.692 | 6 |
| 54 | 1.676 | 2 |
| 55 | 1.661 | 2 |
| 57 | 1.632 | 4 |

TABLE I-continued
X-RAY DIFFRACTION PATTERN FOR ZEOLITE A

| $H^2 + k^2 + l^2$ | d (Å) | 100 I / $I_o$ |
|---|---|---|
| 59 | 1.604 | 6 |

The more significant d values for Zeolite A are given in Table II:

TABLE II
MOST SIGNIFICANT d VALUES FOR ZEOLITE A
d Value of Reflection in A

| | | |
|---|---|---|
| 12.1 | ± | 0.2 |
| 8.7 | ± | 0.2 |
| 7.10 | ± | 0.15 |
| 5.50 | ± | 0.10 |
| 4.10 | ± | 0.10 |
| 3.70 | ± | 0.07 |
| 3.40 | ± | 0.06 |
| 3.29 | ± | 0.05 |
| 2.98 | ± | 0.05 |
| 2.62 | ± | 0.05 |

Occasionally, additional lines not belonging to the pattern for the zeolite appear in a pattern along with the x-ray lines characteristic of that zeolite. This is an indication that one or more additional crystalline materials are mixed with the zeolite in the sample being tested. Small changes in line positions may also occur under these conditions. Such changes in no way hinder the identification of the x-ray patterns as belonging to the zeolite.

The particular x-ray technique and/or apparatus employed, the humidity, the temperature, the orientation of the powder crystals and other variables, all of which are well-known and understood to those skilled in the art of x-ray crystallography or diffraction can cause some variations in the intensities and positions of the lines. These changes, even in those few instances where they become large, pose no problem to the skilled x-ray crystallographer in establishing identities. Thus, the x-ray data given herein to identify the lattice for a zeolite, are not to exclude those materials which, due to some variable mentioned or otherwise known to those skilled in the art, fail to show all of the lines, or show a few extra ones that are permissible in the cubic system of that zeolite, or show a slight shift in position of the lines, so as to give a slightly larger or smaller lattice parameter.

A simpler test described in "American Mineralogist", Vol. 28, page 545, 1943, permits a quick check of the silicon to aluminum ratio of the zeolite. According to the description of the test, zeolite minerals with a three-dimensional network that contains aluminum and silicon atoms in an atomic ratio of $Al/Si = 2/3 = 0.67$, or greater, produce a gel when treated with hydrochloric acid. Zeolites having smaller aluminum to silicone ratios disintegrate in the presence of hydrochloric acid and precipitate silica. These tests were developed with natural zeolites and may vary slightly when applied to synthetic types.

U.S. Pat. No. 2,882,243 describes a process for making Zeolite A comprising preparing a sodium-aluminum-silicate water mixture having an $SiO_2:Al_2O_3$ mole ratio of from 0.5:1 to 1.5:1, and $Na_2O$ mole ratio of from 35:1 to 200:1, maintaining the mixture at a temperature of from 20° C. to 175° C. until Zeolite A is formed, and separating the Zeolite A from the mother liquor.

It is an important object of this invention to provide a method of improving the bone strength or bone quality of animals, including humans, by treatment of the animals with a relatively small amount of metal alumino silicates, especially zeolites.

It is an object of the invention to provide an animal treatment or feed containing zeolite, which inhibits bone disorders in animals, especially humans, such as osteoporosis, osteoarthritis, tibial dyschondroplasia, femur head necrosis and the like.

Another object of the invention is to provide a process for the treatment and/or prevention of bone disorders in animals wherein an effective amount of zeolite is added to the diet of the animal.

It is also an important object of the present invention to provide an improved feed formulation for poultry which contains a small amount of zeolite.

Still another object of the invention is to effectively increase bone strength in animals without causing any deleterious effects in the animals.

Yet a further object of the present invention is to increase the strength of bones in poultry.

Other objects and advantages of the invention will be more fully understood from a reading of the description and claims hereinafter.

SUMMARY OF THE INVENTION

The present invention relates to a method of treating and/or preventing bone disorders such as osteoporosis, osteoarthritis and the like in animals, especially humans, wherein a small amount of zeolite, preferably Zeolite A, is added to the diet of the animal. The zeolite may be administered in tablet or capsule form or as a part of the regular diet of the animal.

DESCRIPTION OF THE PREFERRED EMBODIMENT

It has been discovered that the addition of a relatively small amount of a zeolite, particularly Zeolite A, to a regular or standard feed for animals, especially chickens, effectively improves the bone strength of the animals. Zeolite A is preferably added in amounts of from about 0.25 percent to about 3.00 percent of weight of the total feed, with about 0.5 percent to about 1.5 percent begin especially preferred.

A typical feed preparation for large scale poultry operations comprises the following by weight percent:

| | |
|---|---|
| Corn | 60 |
| Soybean Meal | 30 |
| Limestone | 1 |
| Animal Fat | 4 |
| Phosphates | 1.5 |
| Fish Meal | 2.5 |
| Vitamins, Amino Acids, Salt and Other Minerals | 2 |

Zeolite A is added to such feed formulation in small amounts by weight percent of up to about three. Greater amounts may be used, but may deprive the animals of the desired amount of nutrients. Greater amounts are also likely to be cost ineffective. A preferred amount of Zeolite A is from about 0.25 to about 2.0 percent by weight of the total feed formulation. A most preferred amount of Zeolite A is about 0.5 to about 1.5 weight percent of the total feed formulation.

Using Ethyl EZA ® zeolite, a commercially available Zeolite A, a number of tests were conducted to determine the effect of zeolite on bone strength in chickens.

EXAMPLE 1

Two identical poultry houses each having a capacity for 17,500 broiler chickens were used in a feeding trial. Day-old chicks were fed the following starter diet compositions from day 0 to day 21:

| House #1 (Control House) | |
|---|---|
| Ingredient | Weight Percent |
| Corn | 60.023 |
| Soybean Meal (48.5%) | 29.933 |
| Limestone | 0.849 |
| Dicalcium Phosphate | 1.431 |
| Salt (naCl) | 0.417 |
| Animal Fat | 4.267 |
| MHA (Methionine)[1] | 0.206 |
| Vitamin Mineral Premix[2] | 0.250 |
| Fish Meal (Menhaden) | 2.500 |
| Coban 45[3] | 0.100 |
| Flavomycin[4] | 0.025 |

[1] An amino acid derivative.
[2] Provides the following ingredients per kilogram of feed: Vitamin A, 5512 IU; Vitamin $D_3$, 1653 IU, Vitamin E, IU; riboflavin, 4.4 mg; niacin, 27.6 mg; d-pantothenic acid, 8.8 mg; folic acid, 137.8 mg; Vitamin $B_{12}$, 8.8 mg; choline chloride, 496 mg; ethoxyquin, 55 mg, menadione sodium bisulfite, 1.4 mg; manganese, 66.25 ppm; zinc, 44 ppm; iodine 1.25 ppm; iron, 20 ppm; copper, 2 ppm and cobalt, 0.2 ppm.
[3] A coccidiostat.
[4] An antibacterial feed additive.

House #2 (Experimental House)

The same diet composition as House #1 except that 10 pounds of Zeolite A was added per ton of feed mixed.

The diets were changed at day 21 to a grower diet composition and this diet composition was fed until day 43. The grower diet compositions were as follows:

| House #1 (Control House) | |
|---|---|
| Ingredient | Weight Percent |
| Corn | 65.518 |
| Soybean Meal (48.5% protein) | 24.943 |
| Limestone | 0.832 |
| Dicalcium phosphate | 1.239 |
| Salt (naCl) | 0.419 |
| Animal Fat | 3.965 |
| MHA (Methionine)[1] | 0.208 |
| Vitamin Mineral Premix[2] | 0.250 |
| Fish Meal (Menhaden) | 2.500 |
| Coban 45[3] | 0.100 |
| Flavomycin[4] | 0.025 |

Same footnotes as starter diet composition.

House #2 (Experimental House)

The same grower diet composition as House #1 except that 10 pound of Zeolite A was added per ton of feed mixed.

The diet compositions were again changed at day 43 to a finisher diet composition and this composition was fed until the broilers were ready to be processed for meat, (day 52) except that the feed was allowed to run out about eight hours before the birds were slaughtered. The finisher diet compositions were as follows:

| House #1 (Control House) | |
|---|---|
| Ingredient | Weight Percent |
| Corn | 74.268 |
| Soybean Meal (48.5% Protein) | 18.396 |
| Limestone | 0.615 |
| Dicalcium Phosphate | 0.777 |
| Salt (NaCl) | 0.423 |
| Animal Fat | 2.708 |
| MHA (Methionine)[1] | 0.163 |
| Vitamin Mineral Premix[2] | 0.125 |
| Fish Meal (Menhaden) | 2.500 |
| Coban 45[3] | None |
| Flavomycin[4] | 0.025 |

Same footnotes as for starter and grower diet compositions.

House #2

The same finisher diet composition as for House #1 except that 10 pounds of Zeolite A was added per ton of feed mixed.

The results of this feeding trial indicated the following:

1. Both houses appeared to progress similarly until the middle of the fourth week of age, at which time leg problems began to become evident. A much greater number of broilers in House #1 were affected as determined by the number of birds that would not get up and walk normally when the house was entered.

On day 38, two apparently healthy broilers from each house were necropsied, with the following results: both broilers from the control group (House #1) were found to be in the advanced stage of developing tibial dyschondroplasia. The two experimental birds (House #2) were completely free of the symptoms.

2. The daily mortality rate of the birds in House #1 (Control House) had reached twice the mortality rate of the birds in House #2 (Experimental House) by day 38. The mortality rate for the period from day 28 through the end of the test was 53% higher in the control group. This later period is the one when the broiler mortality was largely due to leg bone problems, a major portion of which were associated with tibial dyschondroplasia.

In addition to the positive effects shown with the leg problems, positive benefits were also indicated in the quality of feathering displayed by the zeolite-fed broilers. Although the results are somewhat subjective, the nutritionist supervising the test, observed that the zeolite-fed broilers had a lot nicer feathering than those broilers not receiving any zeolite. It is well known in the art, that better feathering means higher grade carcasses, less condemnations, less trim loss and higher meat yields. Overall, a higher quality or better broiler is obtained with broilers fed zeolites as opposed to those broilers not receiving zeolites.

EXAMPLE 2

In another feeding trial similar in duration to that of Example 1 but with laying hens, leg bones were analyzed for breaking strength and for calcium and phosphorus content of the bone ash. The results are shown in Table A below:

TABLE A

| Percent Zeolite A in Diet | Breaking Strength (Kg) | Percent Calcium | Percent Phosphorus |
|---|---|---|---|
| 0 | 13.7 | 37.2 | 17.4 |
| 0.5 | 14.2 | 36.7 | 17.7 |
| 1.0 | 14.2 | 37.6 | 18.3 |
| 1.5 | 14.3 | 37.3 | 17.1 |

TABLE A-continued

| Percent Zeolite A in Diet | Breaking Strength (Kg) | Percent Calcium | Percent Phosphorus |
| --- | --- | --- | --- |
| 3.0 | 14.0 | 36.5 | 18.3 |

EXAMPLE 3

In another feeding trial similar to that of Example 2, but with a different age bird, leg bones were again analyzed in the manner of Example 2 with the results shown in Table B hereinafter.

TABLE B

| Percent Zeolite A in Diet | Breaking Strength (Kg) | Percent Calcium | Percent Phosphorus |
| --- | --- | --- | --- |
| 0 | 17.4 | 36.9 | 18.9 |
| 0.75 | 16.9 | 38.1 | 18.7 |
| 1.50 | 17.8 | 38.6 | 18.3 |

The term poultry includes all domestic fowl, namely chickens, turkeys, ducks, geese, and the like.

Corn is the principal ingredient in the diet for most poultry. A feed formulation comprising by weight percent the following is desirable:

|  | Weight Percent |
| --- | --- |
| Corn | 50–75 |
| Soybean Meal | 10–30 |
| Calcium Carbonate | 1.5–10 |
| Zeolite A | 0.25–3.0 |

Milo (grain sorghum) and wheat are sometimes substituted for corn in whole or in part.

Calcium carbonate is usually in the form of natural limestone ground to a suitable particle size, but sometimes oyster shells which have also been suitably ground are used.

It can be appreciated that a wide variety of nutrients or foods may be included in the diets of poultry. In a controlled environment, the poultry are only exposed to desired foods or food products. A typical laying hen ratio composition for example contains the following:

|  |  | Weight Percent |
| --- | --- | --- |
| crude protein | not less than | 16.0 |
| crude fat | not less than | 2.5 |
| crude fiber | not more than | 7.0 |
| calcium (as Ca) | not less than | 3.1 |
| calcium (as Ca) | not more than | 4.1 |
| phosphorus (P) | not less than | 0.5 |
| iodine (I) | not less than | 0.0001 |
| salt (NaCl) | not less than | 0.3 |
| salt (NaCl) | not more than | 0.9 |

The foregoing compositions is obtained from or included the following ingredients:

Grain and Processed Grain By-Products. Including corn, corn hominy, corn germ meal, barley, millet, oats, rice, rice hulls, rye, sorghum, wheat and wheat shorts. These are among the energy ingredients, mostly carbohydrates with some proteins.

Plant Protein Products. Includes soybean oil meal, barley malt sprouts, coconut meal, corn distillers grain, corn gluten meal, cottonseed meal, pea seed, potato meal, peanut meal, rape seed meal, sunflower meal, wheat germ meal, brewers' yeast. All of these are protein sources.

Animal and Fish By-Products. Includes blood meal, blood flour, dried buttermilk, dried whey, dried casein, fish meal, dried fish solubles, liver meal, meat meal, meat meal tankage, bone meal and dried skim milk. Anchovies, herring and menhaden are sources of fish meal.

Minerals and Synthetic Trace Ingredients. Includes vitamins such as B-12, A, pantothenate, niacin, riboflavin, K, etc., DL methionine, choline chloride, folic acid, dicalcium phosphate, magnesium sulfonate, potassium sulfate, calcium carbonate (limestone, oyster shells), salt, sodium selenite, manganous oxide, calcium iodate, copper oxide, zinc oxide and D activated animal sterol.

Molasses and animal fats are added to improve palatability and to increase or balance the energy levels.

Preservatives are also added such as Ethoxyquin TM and sodium sulfite.

In general, a feed composition for laying poultry should preferably contain by weight percent the following:

|  |  | Weight Percent |
| --- | --- | --- |
| crude protein | at least about | 14 |
| crude fat | at least about | 2 |
| crude fiber | not more than about | 7 |
| calcium | about | 2.7 to 4.1 |
| phosphorus | at least about | 0.25 |
| iodine | at least | 0.0001 |
| sodium | about | 0.1 to 0.4 |
| chlorine | about | 0.1 to 0.5 |
| Zeolite A | about | 0.25 to 3.0 |

The administering of zeolites, especially Zeolite A to animals, including humans, cattle, sheep, goats, swine as well as poultry, may be in tablet or capsule form or as part of the regular diet of the animals.

Improved bone strength and calcium related functions in animals is obtained by administration of low levels of zeolite, namely Zeolite A, to the animals.

The invention would be of particular benefit to postmenopausal women who are prone to development of osteoporosis.

Administration of dietary zeolite would benefit patents recovering from bone surgery or broken bones by increasing calcium levels in the blood.

Although the exact mechanism by which the zeolite improves bone strength is unknown, it is believed that the zeolite enables the animals treated to more effectively utilize calcium in their systems.

The invention is also useful in treating diseases and disorders in humans and other animals which are non-bone related. For example, ascites which is the accumulation of fluid in the abdominal cavity, commonly referred to as waterbelly, is a very costly syndrome to the boiler industry. This syndrome which is of hepatic origin may occur to some extent in all animals including man, e.g. as manifested in cirrhosis.

In the broiler industry, the syndrome predominantly affects fast growing birds, especially males, and the condition is most common at high altitudes where atmospheric oxygen partial pressures are reduced. Among other aggravating factors are poor ventilation, cold temperatures, toxins, excess dietary sodium, and excess residues from aromatic hydrocarbon-based insecticides and disinfectants. In addition, ascites may occur along with or as the result of viral and other infections that may be prevalent from time to time.

Ascites in broilers is related clinically to sudden death syndrome in which death occurs primarily from a heart defect. The ascites condition has been shown to be somewhat strain related and is often referred to in oversimplified terms as resulting from the geneticist's development of a bird whose growth is muscular and skeletal capacities has outpaced its growth in pulmonary and vascular system capacities. As demand for oxygen is increased, these systems become over-extended and increases in blood pressure and heart rate result in increased capillary permeabilities. The over-extended system increases the load on the heart, particularly the right ventricle, and the lungs. In many cases, heart failure occurs before large body fluid accumulation has occurred and thus the cause of death is considered sudden death syndrome when in reality it was ascites in its early stages.

EXAMPLE 3

In this example, a study was conducted in a research house on a large broiler farm in Queretaro, Mexico at an altitude of 7700 feet above sea level for a total of eight weeks. The study consisted of 4000 broilers divided into four dietary groups; the groups were further divided into 10 replicate pens, 5 of which received Zeolite A (0.25% in starter, 0.5% in finisher) and 5 of which did not. The four dietary groups varied in energy level from high to low (about 1350, 1340, 1280 and 1240 KCal/lb). The diets were adjusted so that they all contained the same sodium level in order to eliminate the sodium related ascites effect. The cause of death for all of the losses was divided into two categories, ascites and other causes. Weight gain, feed consumption and feed conversion were measured. The data are summarized in Table B, below:

TABLE B

ZEOLITE A FEED COMPONENT BROILER TEST

| Diet | | Mortality % | | | Avg. 8 week Weight lb | Avg. 8 week Feed Reqd lb | Feed Conv. |
|---|---|---|---|---|---|---|---|
| | | Total | Ascites | Other | | | |
| 1350 KCal/lb | Control | 20.10 | 17.14 | 2.96 | 5.195 | 12.29 | 2.366 |
| | Zeolite A | 13.45 | 11.90 | 1.55 | 5.061 | 11.88 | 2.347 |
| 1340 KCal/lb | Control | 31.81 | 27.89 | 3.92 | 5.032 | 12.77 | 2.537 |
| | Zeolite A | 16.81 | 13.65 | 3.16 | 4.803 | 11.69 | 2.434 |
| 1280 KCal/lb | Control | 22.74 | 19.81 | 2.93 | 5.006 | 12.52 | 2.501 |
| | Zeolite A | 18.75 | 16.20 | 2.55 | 4.948 | 12.18 | 2.461 |
| 1240 KCal/lb | Control | 20.12 | 15.43 | 4.69 | 5.065 | 12.85 | 2.537 |
| | Zeolite A | 27.80 | 24.14 | 3.66 | 5.182 | 13.21 | 2.548 |

The results of this trial show that inclusion of Zeolite A in the three highest energy diets results in a reduction in mortality attributable to ascites. The results also show that there is a tendency toward slightly lower body weights in these three diets with Zeolite A inclusion. Since it is known that ascites is not as severe in slower growing birds it might be inferred that this is the reason for the reduced mortality. However, when the lowest energy diet is considered, the Zeolite A-fed birds had the second heaviest body weight in the entire study; this is certainly contrary to what would have been expected from a low energy diet.

While not wishing to be bound by theory, the higher mortality experienced by the Zeolite A-fed birds on the lowest energy diet may be a result of the inclusion of Zeolite A, in a lower energy diet resulting in better energy utilization efficiency and higher growth rate accompanied by a higher incidence of ascites.

Mortality due to all other causes was lower with the Zeolite A diets at all energy levels. This indicates that a general overall improvement in bird health results from dietary Zeolite A use.

The Zeolite A-fed birds in the three higher energy diets converted feed more efficiently than their control counterparts. With the low energy group, the Zeolite A diet was slightly less efficient. The low energy group data was somewhat faulted because of a miscount of the number of chicks placed in one of the replicates and thus the replicate was not counted in the study.

The invention is also useful in increasing the quality of blood of humans and other animals.

EXAMPLE 4

Broiler chickens, fed with a diet containing 0.25 wt. % Zeolite A for the first four weeks and 0.50 wt. % Zeolite A for the next three weeks showed increases in the total nucleated blood cell count, the hemoglobin and the hematocrit as compared to broilers fed the same feed sans Zeolite A. The result is shown in Tables C and Table D, below:

TABLE C

| ZEOLITE A | Total Nucleated Count ($\times 10^6$) | | Hemoglobin (g/dl) | | Hematocrit (%) | |
|---|---|---|---|---|---|---|
| | 28 day | 49 day | 28 day | 49 day | 28 day | 49 day |
| NO | 2.52 ± .04 | 2.63 ± .05 | 9.10 ± .16 | 8.75 ± .27 | 28.8 ± .4 | 28.1 ± .6 |
| YES | 2.64 ± .05 | 2.82 ± .05 | 9.69 ± .18 | 9.06 ± .26 | 30.4 ± .5 | 29.5 ± .6 |
| P of F | .06 | .02 | .02 | .22 | .02 | .08 |

TABLE D

| ZEOLITE A | Total Nucleated Count ($\times 10^6$) | | Hemoglobin (g/dl) | | Hematocrit (%) | |
|---|---|---|---|---|---|---|
| | 28 day | 49 day | 28 day | 49 day | 28 day | 49 day |
| NO | 2.72 ± .04 | 2.76 ± .05 | 9.46 ± .19 | 8.72 ± .26 | 29.9 ± .5 | 28.3 ± .6 |
| YES | 2.65 ± .05 | 2.83 ± .07 | 9.54 ± .17 | 9.22 ± .26 | 29.8 ± .6 | 29.5 ± .7 |

TABLE D-continued

| ZEOLITE | Total Nucleated Count (× 10⁶) | | Hemoglobin (g/dl) | | Hematocrit (%) | |
| --- | --- | --- | --- | --- | --- | --- |
| A | 28 day | 49 day | 28 day | 49 day | 28 day | 49 day |
| P of F | .31 | .43 | .78 | .16 | .79 | .22 | wherein the increases are greater in males than females.

To further demonstrate the improvement in blood quality, adult laying hens (60 weeks old) were tested for eight weeks on a feed including 0.75%, by weight Zeolite A. The result of this study is shown in Table E, below:

TABLE E

White Leghorn Blood Parameters as Affected by Zeolite A Feed Component

| Treatment | n | Total Nucleated Blood Cells (× 10⁶) | Hemoglobin (g/dl) | Hematocrit (%) | Estimated Red Blood Cells (× 10⁶) |
| --- | --- | --- | --- | --- | --- |
| CONTROL | 56 | 2.60 ± 0.03 | 8.20 ± 0.11 | 24.9 ± 0.3 | 2.42 ± 0.04 |
| ZEOLITE A | 55 | 2.67 ± 0.03 | 8.69 ± 0.10 | 25.7 ± 0.3 | 2.47 ± 0.03 |
| P of F | | 0.07 | 0.0017 | 0.0266 | 0.17 |

Again, increases in total nucleated blood cells, hemoglobin and hematocrit were shown.

Finally, sixty-four week old hens were fed for 35 days with feeds comprising 0.75 and 1.50 wt. %. This result is shown in Table F, below:

TABLE F

| Zeolite A | N | Total Nucleated Blood Cells (× 10⁶) | Hemoglobin (g/dl) | Hemocrit (%) | Plasma Proteins (g/100 mL) | Total Red Blood Cells(× 10⁶) |
| --- | --- | --- | --- | --- | --- | --- |
| 0 | 7 | 2.30 ± 0.06 | 8.29 ± 0.22 | 24.8 ± 0.7 | 7.29 ± 0.5 | 2.20 ± 0.06 |
| .75 | 5 | 2.73 ± 0.22 | 8.74 ± 0.30 | 26.6 ± 1.1 | 6.08 ± 0.3 | 2.58 ± 0.20 |
| 1.50 | 7 | 2.39 ± 0.11 | 8.27 ± 0.50 | 24.6 ± 0.4 | 6.91 ± 0.4 | 2.25 ± 0.11 |
| P of F | | .08 | .66 | .41 | .21 | .10 |

The trends in increasing the above-discussed blood parameters were similar.

These same hens were tested to determine the blood cholesterol and the liver fat. As can be seen from the data in Table G, below:

TABLE F

| Fatty Liver | |
| --- | --- |
| % Zeolite in Diet | % Liver Fat |
| 0 | 22.4 ± 2.5 |
| 0.75 | 19.0 ± 1.4 |
| 1.50 | 14.9 ± 1.3 |

| Chicken Blood Cholesterol | |
| --- | --- |
| % Zeolite in Diet | mg/dl Serum Cholesterol |
| 0 | 144 |
| 0.75 | 89 |
| 1.50 | 98 |

Although the invention is particularly directed to zeolites, more particularly Zeolite A, and most particularly to sodium zeolite A, other metal alumino silicates are suitable. The latter include metals of Group 1A such as sodium and potassium and metals of Group IIA such as calcium and magnesium. Examples of such compounds are potassium alumino silicate, sodium alumino silicate, calcium alumino silicate, and magnesium alumino silicate.

The foregoing disclosure and description of the invention is illustrative and explanatory thereof and various changes in the illustrated process may be made within the scope of the appended claims without departing from the spirit of the invention.

We claim:

1. A method of treating ascites in animals wherein a small amount of zeolite is regularly fed to the animal.

2. The method of claim 1 wherein the zeolite is a Zeolite A.

3. The method of claim 1 wherein the zeolite is a sodium Zeolite A.

4. The method of claim 1 wherein the zeolite is a potassium Zeolite A.

5. The method of claim 1 wherein the zeolite is a calcium Zeolite A.

6. The method of claim 1 wherein the amount of Zeolite A fed to the animal is from about 0.25 to about 3 weight percent of the feed fed to the animal.

7. The method of claim 1 wherein the amount of Zeolite A added to the feed of the animal is from about 0.25 percent to about 0.50 percent by weight.

8. The method of claim 1 wherein the animal is human.

9. The method of claim 1 wherein the animal is avian.

10. The method of claim 1, wherein the animal is bovine.

11. The method of claim 1, wherein the animal is canine or feline.

12. The method of claim 1, wherein the animal is ovine.

13. The method of claim 1, wherein the animal is swine.

* * * * *